United States Patent [19]

Kobayashi et al.

[11] Patent Number: 5,631,145
[45] Date of Patent: May 20, 1997

[54] PROCESS FOR PRODUCING HUMAN SERUM ALBUMIN

[75] Inventors: Kaoru Kobayashi; Kenji Tomomitsu; Shinobu Kuwae; Tomoshi Ohya; Toyoo Ohda, all of Osaka, Japan

[73] Assignee: The Green Cross Corporation, Osaka, Japan

[21] Appl. No.: 348,172

[22] Filed: Nov. 28, 1994

[30] Foreign Application Priority Data

Nov. 26, 1993 [JP] Japan ................... 5-296260

[51] Int. Cl.$^6$ ................... C12P 21/00; C12P 21/02; C12N 1/14
[52] U.S. Cl. ................... 435/71.1; 435/69.1; 435/171; 435/911; 435/942
[58] Field of Search ................... 435/71.1, 71.2, 435/69.1, 911, 942

[56] References Cited

U.S. PATENT DOCUMENTS

| | | | |
|---|---|---|---|
| 4,746,608 | 5/1988 | Mizukami et al. | 435/68 |
| 5,330,901 | 7/1994 | Prevatt et al. | 435/69.6 |
| 5,334,512 | 8/1994 | Kobayashi et al. | 435/69.1 |
| 5,369,020 | 11/1994 | Sumi et al. | 435/69.1 |

OTHER PUBLICATIONS

Derwent Abs. WPIL 94:146982/18 Tonen Corp (JP 06090742) Apr. 5, 1994.
Derwent Abs WPIL 94–226852/28 Green Cross Corp (EP–606917) Jul. 20, 1994.
Derwent Abs WPIL 90–093372/13 Fleer et al (FR 2635113) Feb. 9, 1990.
APS Abs (Japan 06–100892) Washimi et al Jul. 13, 1994.

*Primary Examiner*—Herbert J. Lilling
*Attorney, Agent, or Firm*—Sughrue, Mion, Zinn, Macpeak & Seas

[57] ABSTRACT

A process for producing recombinant human serum albumin (HSA) which comprises culturing an HSA producing host prepared by gene manipulation techniques at a temperature of from 21° to 29° C. Culturing the HSA producing host under such a specified temperature condition makes it possible to increase productivity of HSA production, improve the growth yield of an HSA producing host, and reduce the degree of coloring in the HSA preparation.

7 Claims, No Drawings

PROCESS FOR PRODUCING HUMAN SERUM ALBUMIN

FIELD OF THE INVENTION

This invention relates to the improvement of a process for producing human serum albumin (to be referred to as "HSA" hereinafter) by the culturing of a host transformed by means of gene manipulation techniques.

BACKGROUND OF THE INVENTION

HSA is a main component constituting blood plasma and is used in pharmaceutical preparations for the treatment of massive hemorrhage, shock, burns, hypoproteinemia or fetal erythroblastosis.

Currently, HSA is produced mainly as a fractionated product from collected blood. However, such a production process has problems because it is economically disadvantageous and the supply of blood is sporadic. In addition, there may a problem with the blood itself, as blood may contain undesirable substances, such as the hepatitis virus.

The recent development of recombinant DNA techniques has rendered possible the production of various useful polypeptides by microorganisms and cells, and research and development efforts have actively been made on the large scale production of HSA by means of gene manipulation techniques. However, because of low production yields, there still is an unsettled problem concerning the establishment of techniques for high purity, low cost, industrial production of HSA.

The culturing of an HSA producing host prepared by gene manipulation techniques in a medium has been carried out at 30° C. when the host is a yeast strain (JP-A-3-83595 and JP-A-4-299984 corresponding to EP-A-506040; the term "JP-A" as used herein means an "unexamined published Japanese patent application").

SUMMARY OF THE INVENTION

In view of the above circumstances, an object of the present invention is to increase the productivity of HSA production, especially through the improvement of culture conditions.

With the aim of achieving the above object, the inventors of the present invention have conducted intensive studies and found that the productivity of HSA production can be increased, the growth yield of the HSA producing host can be improved and coloring of the product can be inhibited when an HSA producing host prepared by gene manipulation techniques is cultured at a temperature of from 21° to 29° C. The present invention has been accomplished on the basis of this finding.

Accordingly, the present invention provides a process for producing recombinant human serum albumin that comprises culturing a human serum albumin producing host prepared by gene manipulation techniques at a temperature of from 21° to 29° C.

Other objects and advantages of the present invention will be made apparent as the description progresses.

DETAILED DESCRIPTION OF THE INVENTION

The HSA producing host prepared by gene manipulation techniques to be used in the present invention is not particularly limited, provided that it is prepared via gene manipulation techniques, and any of the hosts disclosed in published reports and those which will be developed in the future may be used at will. Illustrative examples of such hosts include cells of microorganisms such as *Escherichia coil*, yeasts or *Bacillus subtills*, as well as animal cells, which have been made into HSA producing cells by gene manipulation techniques. According to the present invention, it is desirable to use a strain of yeast, especially belonging to the genus Saccharomyces, such as *Saccharomyces cerevisiae*, the genus Pichia, such as *Phichia pastoris* or the genus Kluyveromyces, such as *Kluyveromyces lactis*. An auxotrophic strain or an antibiotic sensitive strain may also be used. G 418 sensitive strains such as *Saccharomyces cerevisiae* AH 22 (a, his 4, leu 2, can 1), *Pichia pastoris* GTS 115 (his 4) and *Kluyveromyces lactis* MW98-8C ($\alpha$, uraA, arg, lysk$^+$, pKD1$^0$) may also be used preferably.

Preparation of the HSA producing host, production of HSA by culturing the host, and isolation and collection of HSA from the culture broth, are all carried out in accordance with known methods which may be modified slightly. For example, preparation of an HSA-producing host (or an HSA-producing strain) may be effected using a process in which a natural human serum albumin gene is used (JP-A-58-56684 corresponding to EP-A-73646, JP-A-58-90515 corresponding to EP-A-79739 and JP-A-58-150517 corresponding to EP-A-91527), a process in which a novel human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into a chromosome (JP-A-3-72889 corresponding to EP-A-399455), a process in which hosts are fused (JP-A-3-53877 corresponding to EP-A-409156), a process in which a mutation is generated in a methanol containing medium, a process in which a mutant AOX$_2$ promoter is used (JP-A-4-299984 corresponding to EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-39576 corresponding to EP-A-251744 and U.S. Pat. No. 4,937,193 and JP-A-63-74493 corresponding to EP-A-28637) and a process in which HSA is expressed in Pichia (JP-A-2-104290 corresponding to EP-A-344459).

The process in which a mutation is generated in a methanol-containing medium is carried out in the following manner. First, a 5' non-coding region of the HSA gene is removed from a plasmid pHSA113 containing a transcription unit that is constructed so as to express HSA under the control of an AOX$_1$ promoter (see, JP-A-2-104290 corresponding to EP-A-344459 for the plasmid pHSA113 and JP-A-63-39584 corresponding to EP-A-244598 for the AOX$_1$ promoter) to prepare an HSA expression plasmid pPGP1. Then, the plasmid pPGP1 is integrated into the AOX$_1$ gene region of an appropriate host, preferably a Pichia yeast, more preferably Pichia strain GTS 115 (NRRL deposition number Y-15851) in accordance with a process disclosed in JP-A-2-104290 corresponding to EP-A-344459 to obtain a transformant (PC4130 when Pichia strain GTS 115 is used). Since the thus obtained transformant does not grow well in a methanol-containing medium (Mut$^-$ strain), mutation of the transformant is effected by culturing the transformant in a methanol-containing medium to isolate a mutant strain that is capable of growing in the medium in accordance with a process disclosed in JP-A-4-299984 corresponding to EP-A-506040. The methanol concentration in the medium may be in the range of approximately from 0.0001 to 5% (preferably about 1 to 5%). The medium may be either synthetic or natural, and the culturing may be carried out at 15° to 40° C. (preferably around 30° C.) for 1 to 1,000 hours (preferably about 20 to 120 hours). Examples of the natural culture medium include YP medium (1% yeast extract and 2% polypeptone).

Culturing of an HSA-producing host (an HSA production process) may be carried out using known processes disclosed in the aforementioned references, or in accordance with a process disclosed in JP-A-3-83595 in which high concentration substrate inhibition of HSA producer cells is avoided by gradually adding a high concentration glucose solution to a medium by means of feed batch fermentation, thereby enabling production of both the producer cells and the product in high concentrations, or in accordance with another process disclosed in JP-A-4-293495 corresponding to EP-A-504823 and U.S. Pat. No. 5,334,512, in which productivity of HSA is improved by adding fatty acids to the medium.

Isolation and recovery of HSA may be carried out using known processes disclosed in the aforementioned references, or in accordance with a process disclosed in JP-A-3-103188 corresponding to EP-A-420007 and U.S. Pat. No. 5,132,404, in which proteases are inactivated by heat treatment, or a coloration inhibition process disclosed in JP-A-4-54198 corresponding to U.S. Pat. No. 5,294,699 or EP-A-464590, in which HSA is separated from coloring substances using at least one adsorbent selected from the group consisting of anion exchangers, hydrophobic carriers and activated charcoal.

A medium usually employed in the art can be used as a medium for culturing a transformed host, and culturing of the transformant can be carried out under known conditions. The medium may be either synthetic or natural, but preferably is a liquid medium. For example, a suitable synthetic medium may be composed of: carbon sources, such as various saccharides; nitrogen sources, such as urea, ammonium salts, nitrates; trace nutrients, such as various vitamins, nucleotides; and inorganic salts, such as of Mg, Ca, Fe, Na, K, Mn, Co and Cu. An illustrative example of such a medium is YNB liquid medium, which consists of 0.7% Yeast Nitrogen Base (Difco) and 2% glucose. An illustrative example of a useful natural medium is YPD liquid medium, which consists of 1% Yeast Extract (Difco), 2% Bacto Peptone (Difco) and 2% glucose. The medium pH may be neutral, weakly basic or weakly acidic and preferably ranges from 5.7 to 6.5. In the case of a methylotrophic host, the medium may be further supplemented with methanol in an amount of approximately from 0.01 to 5%.

If only producibility of HSA is taken into consideration, culturing of a host may be carried out at 21° to 29° C., preferably 21° to 28° C., more preferably 21° to 25° C., most preferably 21° to 23° C.

If the culturing temperature is higher than the above range, growth of the host and HSA production are inhibited and the coloration of HSA increases.

When the host is cultured at a temperature lower than the above range, increased cost and a complicated operation are required for controlling the temperature since the culturing is exothermic. Accordingly, for the practical application, the culturing may be carried out at 21° to 29° C., preferably 21° to 28° C., more preferably 23° to 28° C., most preferably 25° to 27° C.

The culturing of the HSA-producing host, for example a yeast strain, within the above temperature range makes it possible to not only increase the yield of HSA 1.3 to 1.5 times but also to decrease the coloration of HSA by 10 to 30%, as compared with the conventional culturing at 30° C.

The culturing period ranges from 1 to 1,000 hours, preferably 20 to 360 hours, by means of static or shake culturing or batch, semi-batch or continuous culturing under agitation and aeration. It is desirable to prepare a seed culture prior to the batch culturing by means of static or shake culturing or batch, semi-batch or continuous culturing under agitation and aeration. The seed culturing may be carried out using the aforementioned YNB liquid medium or YPD liquid medium, preferably at 30° C. (for a yeast host) or 37° C. (for a bacterium host) and for 10 to 100 hours.

After completion of the culturing, HSA is recovered from the resulting culture medium, microbial debris, or cells, in accordance with known isolation and purification methods.

The following examples are provided to further illustrate the present invention. It is to be understood, however, that the examples are for the purpose of illustration only and are not intended as a definition of the limits of the present invention.

EXAMPLE 1

(1) Preparation of an HSA producing host strain

A 5' non-coding region of the HSA gene was removed from a plasmid pHSA113 described in JP-A-2-104290 corresponding to EP-A-344459 containing a transcription unit that is constructed so as to express HSA under the control of an $AOX_1$ promoter to prepare an HSA expression plasmid pPGP1. Then, in accordance with a process disclosed in JP-A-2-104290 corresponding to EP-A-344459, the HSA expression plasmid pPGP1 was digested with NotI and the resulting NotI-digested fragment was substituted for the $AOX_1$ gene region of a *Pichia pastoris* strain GTS115 (his4) to prepare a transformant PC4130. The strain does not grow well in a medium containing methanol as the carbon source (Mut⁻ strain), because of the deletion of the $AOX_1$ gene.

The strain PC4130 was inoculated into 3 ml of YPD medium (1% yeast extract, 2% Bacto Peptone and 2% glucose). After 24 hours of culturing, the cells were inoculated into 50 ml of YPD medium so that the cell density had an initial turbidity corresponding to an $OD_{540}$ of 0.1. After 3 days of culturing at 30° C., the resulting cells were again inoculated into 50 ml of YPD medium at an initial cell turbidity of 0.1 at $OD_{540}$. Thereafter, such subculturing was repeated every 3 days in the same manner. After each subculturing, cells were diluted with sterile water and poured onto a 2% MeOH-YNBw/oa.a. plate (0.7% Yeast Nitrogen Base without Amino Acids, 2% methanol and 1.5% agar powder) in an inoculum size of $10^7$ cells/plate, followed by 5 days of culturing at 30° C. to judge the presence or absence of colonies. Twenty colonies were found on the 2% MeOH-YNBw/oa.a. plate after 12 days of successive subculturing. Mut⁻ strains can hardly grow on the 2% MeOH-YNBw/oa.a. medium, while Mut⁺ strains can grow well. That is, the advent of a colony means that the strain because Mut⁺ and acquired the capacity for increased methanol assimilation. One of the thus obtained colonies was diluted appropriately with sterile water and spread onto a 2% MeOH-YNBw/oa.a. plate to isolate single colonies. One of the resulting single colonies was named GCP101.

An HSA expression plasmid pMM042 was constructed using an $AOX_2$ promoter [a mutant of the natural $AOX_2$ promoter (*YEAST*, 5 167–177, 1988; *Mol. Cell. Biol.*, 9, 1316–1323, 1989), in which the 255th base upstream from the initiation codon of said promoter is changed from T to C] isolated from the strain GCP101. The thus constructed plasmid was introduced into *Pichia pastoris* GTS 115 to obtain a transformant UHG42-3 (EP-A-506040).

(2) Composition of medium

YPD medium (2% Bacto-Peptone, 1% yeast extract and 2% glucose) was used for the seed culture. The compositions of the batch culture medium and the feed medium are shown in Table 1 and Table 2, respectively.

TABLE 1

Composition of the batch culture medium

| Components | Amount per liter |
|---|---|
| Glycerol | 50.0 g |
| $H_3PO_4$ (85%) | 14.0 ml |
| $CaSO_4.2H_2O$ | 0.6 g |
| $K_2SO_4$ | 9.5 g |
| $MgSO_4.7H_2O$ | 7.8 g |
| KOH | 2.6 g |
| Biotin solution *1 | 1.6 ml |
| YTM solution *2 | 4.4 ml |

*1 Biotin solution: 0.2 g/l
*2 YTM solution has the following composition:

| Components | Amount per liter |
|---|---|
| $FeSO_4.7H_2O$ | 65.0 g |
| $CuSO_4.5H_2O$ | 6.0 g |
| $ZnSO_4.7H_2O$ | 20.0 g |
| $MnSO_4.4-5H_2O$ | 3.0 g |
| $H_2SO_4$ | 5.0 ml |

TABLE 2

Composition of the feed medium

| Components | Amount |
|---|---|
| YTM solution | 2 ml |
| Methanol | 1,000 ml |

(3) Culturing method using 3 liter-fermentor

1) Seed culture

A 1 ml portion of the strain UHG42-3 contained in a frozen stock vial was inoculated into a 300 ml baffled Erlenmeyer flask containing 50 ml of YPD medium and cultured at 30° C. for 24 hours under shaking. After 24 hours of the culturing, a 14 ml portion of the culture broth was inoculated into 700 ml of the batch culture medium.

2) Main culture

A 14 ml portion of the seed culture broth was inoculated into a 3 liter mini-jar fermentor containing 700 ml of the batch culture medium and subjected to aerated agitation culturing. Separate main cultures were carried out at culture temperatures of 21°, 23°, 25°, 27°, 28° and 30° C. The lower and upper limits of the agitation rate were set to 200 rpm and 1,000 rpm, respectively. The main culturing was carried out by controlling the amount of dissolved oxygen in the medium to be approximately 50% of the saturated dissolved oxygen concentration. When the glycerol in the batch culture medium was consumed, addition of a feeding medium was started. The medium pH was controlled at a constant level of 6.2. Defoaming was effected by adding an antifoaming agent to the medium when required. The culturing was carried out for 360 hours.

(4) Culturing Method Using 1200 Liter-Fermentor

1) First seed culture

A 1 ml portion of the strain UHG42-3 which had been frozen in glycerol was inoculated into a 1,000 ml baffled Erlenmeyer flask containing 200 ml of YPD medium and cultured at 30° C. for 24 hours with shaking.

2) Second seed culture

The first seed culture broth was inoculated into a 10 liter-jar fermentor containing 5 liters of YPD medium, and the second seed culturing was carried out at 30° C. for 24 hours with agitation. The culturing was carried out by controlling the amount of dissolved oxygen in the medium to be approximately 50% of the saturated dissolved oxygen concentration. In the seed culturing, the pH of the medium was not controlled.

3) Main culture

The second seed culture broth was transferred into a 1,200 liter-fermentor containing 250 liters of a batch culture medium and subjected to aerated agitation culturing. Separate main cultures were carried out at culture temperatures of 23°, 25°, 27°, 29° and 30° C. The agitation rate was controlled so that the level of dissolved oxygen in the medium was maintained at approximately 50 to 30% of the saturated dissolved oxygen concentration. When the glycerol in the batch culture medium was consumed, addition of a feeding medium was started. The medium pH was controlled at a fixed level of 5.85. For defoamation of the culture medium, an antifoaming agent was added when required. The culturing was carried out for 360 hours.

TEST EXAMPLE 1

Measurement of cell density

At each culture temperature carried out in Example 1, the culture broth was sampled periodically. Each of the thus collected samples was diluted with distilled water to such a level that the $OD_{540}$ value at the time of measurement was adjusted to 0.3 or less, and then the absorbance of the diluted sample at 540 nm was measured using a spectrophotometer (UV 200, manufactured by Shimadzu Corp.). In this test, the amount of dry cells in each sample was calculated from the absorbance based on a formula $OD_{540}/5.2$. The maximum cell concentration at each culture temperature is shown in Table 3 and Table 4.

TEST EXAMPLE 2

Evaluation of yield of HSA and degree of coloring

At each culture temperature carried out in Example 1, the culture broth was sampled periodically, and each of the thus collected samples was centrifuged at 15,000 rpm for 5 minutes. The resulting supernatant was filtered through Ultra Free C3HV (a 0.45 µm filter for sterilization manufactured by Millipore Products) and subjected to HPLC gel filtration analysis under the following conditions.

Column: Tosoh TSK gel $G3000SW_{xl}$

Mobile phase: 0.3M NaCl, 50 mM Na-Phosphate, 0.1% $NaN_3$, pH 6.5

Flow rate: 0.7 ml/min

Injection: 50 ml

Detection: $A_{280}$, $A_{350}$ (dual wave length)

Results of the evaluation of the yield of HSA and degree of coloring are shown in Table 3 and Table 4. The yield of HSA is expressed as the percentage of total HSA production (g) at each culture temperature when the total HSA production (g) cultured at 30° C. was set as 100%.

Absorbances at 350 nm and 280 nm were measured for each of the cultures just before the completion of the culturing (after 359 hours) to evaluate the degree of coloring as $A_{350}/A_{280}$.

TABLE 3

| Temp. (°C.) | Maximum cell density (g DCW/L) | HSA yield (%) | Degree of coloring ($A_{350}/A_{280}$) |
| --- | --- | --- | --- |
| 30 | 133.7 | (100) | 0.105 |
| 28 | 141.7 | 130 | 0.086 |
| 27 | 148.7 | 129 | 0.083 |
| 25 | 159.4 | 132 | 0.076 |
| 23 | 171.5 | 132 | 0.088 |
| 21 | 177.6 | 148 | 0.084 |

TABLE 4

| Temp. (°C.) | Maximum cell density (g DCW/L) | HSA yield (%) | Degree of coloring ($A_{350}/A_{280}$) |
| --- | --- | --- | --- |
| 30 | 123.7 | (100) | 0.100 |
| 29 | 125.9 | 124 | 0.089 |
| 27 | 119.0 | 139 | 0.090 |
| 25 | 128.8 | 154 | 0.081 |
| 23 | 144.3 | 156 | 0.082 |

According to the present invention, the HSA productivity of a host obtained by gene manipulation techniques can be increased by culturing the host at a temperature of from 21° to 29° C. Culturing under this condition can also improve the growth yield of the HSA producing host, as well as reduce the degree of coloring of the HSA preparation.

While the instant invention has been described in detail and with reference to specific embodiments thereof, it will be apparent to one skilled in the art that various changes and modifications can be made therein without departing from the spirit and scope thereof.

What is claimed is:

1. A process for producing recombinant human serum albumin which comprises culturing a human serum albumin producing host at a temperature of from 21° to 29° C., wherein the human serum albumin producing host is a strain of yeast of the genus Kluyveromyces.

2. The process of claim 1, wherein the human serum albumin producing host is cultured at a temperature of from 21° to 28° C.

3. The process of claim 1, wherein the human serum albumin producing host is cultured at a temperature of from 21° to 25° C.

4. The process of claim 1, wherein the human serum albumin producing host is cultured at a temperature of from 21° to 23° C.

5. The process of claim 1, wherein the human serum albumin producing host is cultured at a temperature of from 23° to 28° C.

6. The process of claim 1, wherein the human serum albumin producing host is cultured at a temperature of from 25° to 27° C.

7. A process for producing recombinant human serum albumin which comprises culturing a human serum albumin producing host at a temperature of from 21° to 29° C., wherein the human serum albumin producing host is derived from *Saccharomyces cerevisiae* AH22.

* * * * *